(12) United States Patent
Wang et al.

(10) Patent No.: US 7,517,677 B2
(45) Date of Patent: Apr. 14, 2009

(54) RECOMBINANT D-AMINO ACID OXIDASES

(76) Inventors: Jun Wang, 23D, Block 5, Royal Ascort, Fo Tan, N.T., Hong Kong (CN); Hongkin Yap, 81B, Yuen Leng Village, Tai Po, N.T., Hong Kong (CN); Waikei Tsang, 2101, Ming Cheong House, Ming Nga Court, Tai Po, New Territories, Hong Kong (CN); Yuksun Lui, Room A2, Blk A, 6/F, Hutchision Estate, 2 Lei Muk Road, Kwai Chung, New Territories, Hong Kong (CN); Yaulung Philip Siu, Flat G, 16/F, Fung Cheung House, 17 Wan Fung Street, Wong Tai Sin, Kowloon Hong Kong (CN); Supyin Tsang, Flat, D, 7/F, On Tai Building, 68 Mei King Street, Tokwawan, Kowloon, Hong Kong (CN); Minghon Yau, 10H, Blk 1, Cheerful Park, Sheung Shui, New Territories, Hong Kong (CN)

( * ) Notice: Subject to any disclaimer, the term of this patent is extended or adjusted under 35 U.S.C. 154(b) by 0 days.

(21) Appl. No.: 11/547,639

(22) PCT Filed: Apr. 12, 2004

(86) PCT No.: PCT/CN2004/000340

§ 371 (c)(1),
(2), (4) Date: Nov. 30, 2006

(87) PCT Pub. No.: WO2005/098000

PCT Pub. Date: Oct. 20, 2005

(65) Prior Publication Data

US 2008/0009052 A1      Jan. 10, 2008

(30) Foreign Application Priority Data

Apr. 8, 2004   (CN) .................. 2004 1 0030842

(51) Int. Cl.
  *C12N 9/04* (2006.01)
  *C12N 15/00* (2006.01)
  *C12N 1/20* (2006.01)
  *C07H 21/04* (2006.01)

(52) U.S. Cl. ................. 435/190; 435/252.3; 435/320.1; 536/23.2

(58) Field of Classification Search ................. 435/190, 435/252.3, 320.1; 536/23.2
  See application file for complete search history.

(56) References Cited

U.S. PATENT DOCUMENTS 6,635,458 B2 * 10/2003 Garcia Lopez et al. ...... 435/190

FOREIGN PATENT DOCUMENTS

| CN | 1087118 A | 5/1994 |
|----|-----------|--------|
| CN | 1246147 A | 3/2000 |
| EP | 0 969 088 A1 | 1/2000 |
| EP | 1 344 830 A1 | 9/2003 |
| JP | 62-262994 A | 11/1987 |
| JP | 63-71180 A | 3/1998 |

OTHER PUBLICATIONS

Pollegiono L., et al., "Characterization of D-Amino Acid Oxidase From *Trigonopsis variabilis*", *Biochemistry and Molecular Biology International*, vol. 31, No. 4, pp. 709-717, (Nov. 1993).

Golini, P., et al., "Immobilization of D-Amino Acid Oxidase From Different Yeasts: Characterization and Application in The Deamination of Cephalosporin C", *Enzyme and Microbial Technology*, vol. 17, No. 4, pp. 324-329, (1995).

Weiquan, L., et al., "Protoplast Formation, Regeneration and Fusion of *Trigonopsis Variabilis*", *Acta Microbiologica Sinica*, vol. 31, No. 3, p. 251-253, (1991).

Simonetta, M.P., et al., "Purification and properties of D-amino-acid oxidase, an inducible flavoenzyme from *Rhoadotorula gracilis*", *Biochimica et Biophysica Acta*, vol. 914, p. 136-142, (1987).

González, F.J., et al., "Molecular Cloning of *TvDAO1*, a Gene Encoding a $_D$-Amino Acid Oxidase from *Trigonopsis variabilis* and its Expression in *Saccharomyces cerevisiae* and *Kluyveromyces lactis*,", *Yeast*, vol. 13, p. 1399-1408, (1997).

Horton, R.M., "In Vitro Recombination and Mutagenesis of DNA", *Methods in Molecular Biology*, vol. 15, p. 251-261 (1993).

Ho, S.N., et al., "Site-directed mutagenesis by overlap extension using the polymerase chain reaction", *Gene*, vol. 77, p. 51-59, (1989).

Alonso, J., et al., "$_D$-Amino-acid oxidase gene from *Rhodotorula gracilis* (*Rhodosporidium toruloides*)", *Microbiology*, vol. 144, p. 1095-1101, (1998).

Isogai, T., et al., "Structure and Expression of cDNA for $_D$-Amino Acid Oxidase Active against Cephalosporin C from *Fusarium solani*", *J. Biochem.*, vol. 108, p. 1063-1069, (1990).

Miyake, Y., et al., "Crystallization and some properties of $_D$-Amino Acid Oxidase Apoenzyme", *Biochemica et Biophysica Acta*, vol. 105, p. 86-99, (1965).

* cited by examiner

*Primary Examiner*—Tekchand Saidha
(74) *Attorney, Agent, or Firm*—The Nath Law Group (57) ABSTRACT

The present invention discloses two novel D-amino acid oxidases, whose activities of converting cephalosporin C to glutaryl-7-aminocephalosporanic acid are at least 25% higher than that of wild-type *Trigonopsis variabilis* D-amino acid oxidase and the encoding DNA sequences thereof.

11 Claims, 3 Drawing Sheets

Fig. 1: Restriction map of plasmid pRSET-kan.

Fig. 2 shows DNA sequence of plasmid pRSET-kan (SEQ ID NO: 13)

```
GATCTCGATCCCGCGAAATTAATACGACTCACTATAGGGAGACCACAACGGTTTCCCTCTAGAAATAATTTTG
TTTAACTTTAAGAAGGAGATATACATATGCGGGGTTCTCATCATCATCATCATCATGGTATGGCTAGCATGAC
TGGTGGACAGCAAATGGGTCGGGATCTGTACGACGATGACGATAAGGATCGATGGGGATCCGAGCTCGAGAT
CTGCAGCTGGTACCATGGAATTCGAAGCTTGATCCGGCTGCTAACAAAGCCCGAAAGGAAGCTGAGTTGGCT
GCTGCCACCGCTGAGCAATAACTAGCATAACCCCTTGGGGCCTCTAAACGGGTCTTGAGGGGTTTTTTGCTGA
AAGGAGGAACTATATCCGGATCTGGCGTAATAGCGAAGAGGCCCGCACCGATCGCCCTTCCCAACAGTTGCG
CAGCCTGAATGGCGAATGGGACGCGCCCTGTAGCGGCGCATTAAGCGCGGCGGGTGTGGTGGTTACGCGCAG
CGTGACCGCTACACTTGCCAGCGCCCTAGCGCCCGCTCCTTTCGCTTTCTTCCCTTCCTTTCTCGCCACGTTCGC
CGGCTTTCCCCGTCAAGCTCTAAATCGGGGGCTCCCTTTAGGGTTCCGATTTAGTGCTTTACGGCACCTCGACC
CCAAAAAACTTGATTAGGGTGATGGTTCACGTAGTGGGCCATCGCCCTGATAGACGGTTTTTCGCCCTTTGAC
GTTGGAGTCCACGTTCTTTAATAGTGGACTCTTGTTCCAAACTGGAACAACACTCAACCCTATCGCGGTCTATT
CTTTTGATTTATAAGGGATTTTGCCGATTTCGGCCTATTGGTTAAAAAATGAGCTGATTTAACAAATATTTAAC
GCGAATTTTAACAAAATATTAACGCTTACAATTTAGGTGGCACTTTTCGGGGAAATGTGCGCGGAACCCCTAT
TTGTTTATTTTTCTAAATACATTCAAATATGTATCCGCTCATGAGACAATAACCCTGATAAATGCTTCAATAAT
ATTGAAAAAGGAAGAGTATGAGTCATATTCAACGGGAAACGTCTTGCTCTAGGCCGCGATTAAATTCCAACAT
GGATGCTGATTTATATGGGTATAAATGGGCTCGCGATAATGTCGGGCAATCAGGTGCGACAATCTATCGATTG
TATGGGAAGCCCGATGCGCCAGAGTTGTTTCTGAAACATGGCAAAGGTAGCGTTGCCAATGATGTTACAGATG
AGATGGTCAGACTAAACTGGCTGACGGAATTTATGCCTCTTCCGACCATCAAGCATTTTATCCGTACTCCTGAT
GATGCATGGTTACTCACCACTGCGATCCCCGGGAAAACAGCATTCCAGGTATTAGAAGAATATCCTGATTCAG
GTGAAAATATTGTTGATGCGCTGGCAGTGTTCCTGCGCCGGTTGCATTCGATTCCTGTTTGTAATTGTCCTTTT
AACAGCGATCGCGTATTTCGTCTCGCTCAGGCGCAATCACGAATGAATAACGGTTTGGTTGATGCGAGTGATT
TTGATGACGAGCGTAATGGCTGGCCTGTTGAACAAGTCTGGAAAGAAATGCATAAACTTTTGCCATTCTCACC
GGATTCAGTCGTCACTCATGGTGATTTCTCACTTGATAACCTTATTTTTGACGAGGGGAAATTAATAGGTTGTA
TTGATGTTGGACGAGTCGGAATCGCAGACCGATACCAGGATCTTGCCATCCTATGGAACTGCCTCGGTGAGTT
TTCTCCTTCATTACAGAAACGGCTTTTTCAAAAATATGGTATTGATAATCCTGATATGAATAAATTGCAGTTTC
ATTTGATGCTCGATGAGTTTTTCTAACTGTCAGACCAAGTTTACTCATATATACTTTAGATTGATTTAAAACTT
CATTTTTAATTTAAAAGGATCTAGGTGAAGATCCTTTTTGATAATCTCATGACCAAAATCCCTTAACGTGAGTT
TTCGTTCCACTGAGCGTCAGACCCCGTAGAAAAGATCAAAGGATCTTCTTGAGATCCTTTTTTTCTGCGCGTAA
TCTGCTGCTTGCAAACAAAAAAACCACCGCTACCAGCGGTGGTTTGTTTGCCGGATCAAGAGCTACCAACTCT
TTTTCCGAAGGTAACTGGCTTCAGCAGAGCGCAGATACCAAATACTGTCCTTCTAGTGTAGCCGTAGTTAGGC
CACCACTTCAAGAACTCTGTAGCACCGCCTACATACCTCGCTCTGCTAATCCTGTTACCAGTGGCTGCTGCCAG
TGGCGATAAGTCGTGTCTTACCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGAACTGAGATACCTACAGCGTGA
GCTATGAGAAAGCGCCACGCTTCCCGAAGGGAGAAAGGCGGACAGGTATCCGGTAAGCGGCAGGGTCGGAA
CAGGAGAGCGCACGAGGGAGCTTCCAGGGGGAAACGCCTGGTATCTTTATAGTCCTGTCGGGTTTCGCCACCT
CTGACTTGAGCGTCGATTTTTGTGATGCTCGTCAGGGGGCGGAGCCTATGGAAAAACGCCAGCAACGCGGC
CTTTTTACGGTTCCTGGGCTTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACCGAGCGCAGCGAGTCAGTG
AGCGAGGAAGCGGAAGAGCGCCCAATACGCAAACCGCCTCTCCCCGCGCGTTGGCCGATTCATTAATGCAG
```

Fig. 3:

SEQUENCE LISTING

<160> NUMBER OF SEQ ID NOS: 18

<210> SEQ ID NO 1
<211> LENGTH: 1071
<212> TYPE: DNA
<213> ORGANISM: Trigonopsis variabilis

<400> SEQUENCE: 1

```
atggctaaaa tcgttgttat tggtgccggt gttgccggtt taactacagc tcttcaactt      60
cttcgtaaag gacatgaggt tacaattgtg tccgagttta cgcccggtga tcttagtatc     120
ggatatacct cgccttgggc aggtgccaac tggctcacat tttacgatgg aggcaagtta     180
gccgactacg atgccgtctc ttatcctatc ttgcgagagc tggctcgaag cagccccgag     240
gctggaattc gactcatcaa ccaacgctcc catgttctca agcgtgatct tcctaaactg     300
gaaggtgcca tgtcggccat ctgtcaacgc aacccctggt tcaaaaacac agtcgattct     360
ttcgagatta tcgaggacag gtccaggatt gtccacgatg atgtggctta tctagtcgaa     420
tttgcttccg tttgtatcca caccggagtc tacttgaact ggctgatgtc ccaatgctta     480
tcgctcggcg ccacggtggt taaacgtcga gtgaaccata tcaaggatgc caattttcta     540
cactcctcag gatcacgccc cgacgtgatt gtcaactgta gtggtctctt tgcccggttc     600
ttgggaggcg tcgaggacaa gaagatgtac cctattcgag gacaagtcgt ccttgttcga     660
aactctcttc cttttatggc ctcctttttcc agcactcctg aaaaagaaaa tgaagacgaa     720
gctctatata tcatgacccg attcgatggt acttctatca ttggcggttg tttccaatcc     780
aacaactggt catccgaacc cgatccttct ctcacccatc gaatcctgtc tagagccctc     840
gaccgattcc cggaactgac caaagatggc cctcttgaca ttgtgcgcga atgcgttggc     900
caccgtcctg gtagagaggg cggtccccga gtagaattag agaagatccc cggcgttggc     960
tttgttgtcc ataactatgg tgccgccggt gctggttacc agtcctctta cggcatggct    1020
gatgaagctg tttcttacgt cgaaagagct cttactcgtc caaacctttta g            1071
```

<210> SEQ ID NO 2
<211> LENGTH: 356
<212> TYPE: PRT
<213> ORGANISM: Trigonopsis variabilis

<400> SEQUENCE: 2

Met Ala Lys Ile Val Val Ile Gly Ala Gly Val Ala Gly Leu Thr Thr

```
                1               5              10              15
Ala Leu Gln Leu Leu Arg Lys Gly His Glu Val Thr Ile Val Ser Glu
                20                      25                  30

Phe Thr Pro Gly Asp Leu Ser Ile Gly Tyr Thr Ser Pro Trp Ala Gly
            35                      40                  45

Ala Asn Trp Leu Thr Phe Tyr Asp Gly Gly Lys Leu Ala Asp Tyr Asp
        50                      55                  60

Ala Val Ser Tyr Pro Ile Leu Arg Glu Leu Ala Arg Ser Ser Pro Glu
65                      70                  75                  80

Ala Gly Ile Arg Leu Ile Asn Gln Arg Ser His Val Leu Lys Arg Asp
                85                      90                  95

Leu Pro Lys Leu Glu Gly Ala Met Ser Ala Ile Cys Gln Arg Asn Pro
            100                     105                 110

Trp Phe Lys Asn Thr Val Asp Ser Phe Glu Ile Ile Glu Asp Arg Ser
        115                     120                 125

Arg Ile Val His Asp Asp Val Ala Tyr Leu Val Glu Phe Ala Ser Val
    130                     135                 140

Cys Ile His Thr Gly Val Tyr Leu Asn Trp Leu Met Ser Gln Cys Leu
145                     150                 155                 160

Ser Leu Gly Ala Thr Val Val Lys Arg Val Asn His Ile Lys Asp
                165                     170                 175

Ala Asn Phe Leu His Ser Ser Gly Ser Arg Pro Asp Val Ile Val Asn
            180                     185                 190

Cys Ser Gly Leu Phe Ala Arg Phe Leu Gly Gly Val Glu Asp Lys Lys
        195                     200                 205

Met Tyr Pro Ile Arg Gly Gln Val Val Leu Val Arg Asn Ser Leu Pro
    210                     215                 220

Phe Met Ala Ser Phe Ser Ser Thr Pro Glu Lys Glu Asn Glu Asp Glu
225                     230                 235                 240

Ala Leu Tyr Ile Met Thr Arg Phe Asp Gly Thr Ser Ile Ile Gly Gly
                245                     250                 255

Cys Phe Gln Ser Asn Asn Trp Ser Ser Glu Pro Asp Pro Ser Leu Thr
            260                     265                 270

His Arg Ile Leu Ser Arg Ala Leu Asp Arg Phe Pro Glu Leu Thr Lys
        275                     280                 285

Asp Gly Pro Leu Asp Ile Val Arg Glu Cys Val Gly His Arg Pro Gly
    290                     295                 300

Arg Glu Gly Gly Pro Arg Val Glu Leu Glu Lys Ile Pro Gly Val Gly
305                     310                 315                 320

Phe Val Val His Asn Tyr Gly Ala Ala Gly Ala Gly Tyr Gln Ser Ser
                325                     330                 335

Tyr Gly Met Ala Asp Glu Ala Val Ser Tyr Val Glu Arg Ala Leu Thr
            340                     345                 350

Arg Pro Asn Leu
        355

<210> SEQ ID NO 3
<211> LENGTH: 1071
<212> TYPE: DNA
<213> ORGANISM: Trigonopsis variabilis

<400> SEQUENCE: 3
atggctaaaa tcgttgttat tggtgccggt gttgccggtt taactacagc tcttcaactt      60
cttcgtaaag gacatgaggt tacaattgtg tccgagttta cgcccggtga tcttagtatc     120
```

```
ggatatacct cgccttgggc aggtgccaac tggctcccgt tttacgatgg aggcaagtta    180
gccgactacg atgccgtctc ttatcctatc ttgcgagagc tggctcgaag cagccccgag    240
gctggaattc gactcatcaa ccaacgctcc catgttctca agcgtgatct tcctaaactg    300
gaaggtgcca tgtcggccat ctgtcaacgc aaccctggt tcaaaaacac agtcgattct    360
ttcgagatta tcgaggacag gtccaggatt gtccacgatg atgtggctta tctagtcgaa    420
tttgcttccg tttgtatcca caccggagtc tacttgaact ggctgatgtc ccaatgctta    480
tcgctcggcg ccacggtggt taaacgtcga gtgaaccata tcaaggatgc cattttcta    540
cactcctcag gatcacgccc cgacgtgatt gtcaactgta gtggtctctt gcccggttc    600
ttgggaggcg tcgaggacaa gaagatgtac cctattcgag acaagtcgt ccttgttcga    660
aactctcttc cttttatggc ctccttttcc agcactcctg aaaagaaaa tgaagacgaa    720
gctctatata tcatgacccg attcgatggt acttctatca ttggcggttg tttccaatcc    780
aacaactggt catccgaacc cgatccttct ctcacccatc gaatcctgtc tagagccctc    840
gaccgattcc cggaactgac caaagatggc cctcttgaca ttgtgcgcga atgcgttggc    900
caccgtcctg gtagagaggg cggtcccga gtagaattag agaagatccc cggcgttggc    960
tttgttgtcc ataactatgg tgccgccggt gctggttacc agtcctctta cggcatggct   1020
gatgaagctg tttcttacgt cgaaagagct cttactcgtc aaacctttta g             1071
```

<210> SEQ ID NO 4
<211> LENGTH: 356
<212> TYPE: PRT
<213> ORGANISM: Trigonopsis variabilis

<400> SEQUENCE: 4

```
Met Ala Lys Ile Val Ile Gly Ala Gly Val Ala Gly Leu Thr Thr
1               5                   10                  15

Ala Leu Gln Leu Leu Arg Lys Gly His Glu Val Thr Ile Val Ser Glu
                20                  25                  30

Phe Thr Pro Gly Asp Leu Ser Ile Gly Tyr Thr Ser Pro Trp Ala Gly
            35                  40                  45

Ala Asn Trp Leu Pro Phe Tyr Asp Gly Gly Lys Leu Ala Asp Tyr Asp
        50                  55                  60

Ala Val Ser Tyr Pro Ile Leu Arg Glu Leu Ala Arg Ser Ser Pro Glu
65                  70                  75                  80

Ala Gly Ile Arg Leu Ile Asn Gln Arg Ser His Val Leu Lys Arg Asp
                85                  90                  95

Leu Pro Lys Leu Glu Gly Ala Met Ser Ala Ile Cys Gln Arg Asn Pro
            100                 105                 110

Trp Phe Lys Asn Thr Val Asp Ser Phe Glu Ile Ile Glu Asp Arg Ser
        115                 120                 125

Arg Ile Val His Asp Asp Val Ala Tyr Leu Val Glu Phe Ala Ser Val
    130                 135                 140

Cys Ile His Thr Gly Val Tyr Leu Asn Trp Leu Met Ser Gln Cys Leu
145                 150                 155                 160

Ser Leu Gly Ala Thr Val Val Lys Arg Arg Val Asn His Ile Lys Asp
                165                 170                 175

Ala Asn Phe Leu His Ser Ser Gly Ser Arg Pro Asp Val Ile Val Asn
            180                 185                 190

Cys Ser Gly Leu Phe Ala Arg Phe Leu Gly Gly Val Glu Asp Lys Lys
        195                 200                 205
```

```
Met Tyr Pro Ile Arg Gly Gln Val Val Leu Val Arg Asn Ser Leu Pro
    210                 215                 220

Phe Met Ala Ser Phe Ser Ser Thr Pro Glu Lys Glu Asn Glu Asp Glu
225                 230                 235                 240

Ala Leu Tyr Ile Met Thr Arg Phe Asp Gly Thr Ser Ile Ile Gly Gly
                245                 250                 255

Cys Phe Gln Ser Asn Asn Trp Ser Ser Glu Pro Asp Pro Ser Leu Thr
            260                 265                 270

His Arg Ile Leu Ser Arg Ala Leu Asp Arg Phe Pro Glu Leu Thr Lys
        275                 280                 285

Asp Gly Pro Leu Asp Ile Val Arg Glu Cys Val Gly His Arg Pro Gly
    290                 295                 300

Arg Glu Gly Gly Pro Arg Val Glu Leu Glu Lys Ile Pro Gly Val Gly
305                 310                 315                 320

Phe Val Val His Asn Tyr Gly Ala Ala Gly Ala Gly Tyr Gln Ser Ser
                325                 330                 335

Tyr Gly Met Ala Asp Glu Ala Val Ser Tyr Val Glu Arg Ala Leu Thr
            340                 345                 350

Arg Pro Asn Leu
        355

<210> SEQ ID NO 5
<211> LENGTH: 1071
<212> TYPE: DNA
<213> ORGANISM: Trigonopsis variabilis

<400> SEQUENCE: 5
atggctaaaa tcgttgttat tggtgccggt gttgccggtt taactacagc tcttcaactt        60
cttcgtaaag acatgaggt tacaattgtg tccgagttta cgcccggtga tcttagtatc       120
ggatatacct cgccttgggc aggtgccaac tggctcagct tttacgatgg aggcaagtta       180
gccgactacg atgccgtctc ttatcctatc ttgcgagagc tggctcgaag cagccccgag       240
gctggaattc gactcatcaa ccaacgctcc catgttctca gcgtgatct tcctaaactg        300 gaaggtgcca tgtcggccat ctgtcaacgc aaccctggt caaaaacac agtcgattct        360 ttcgagatta tcgaggacag gtccaggatt gtccacgatg atgtggctta tctagtcgaa       420
tttgcttccg tttgtatcca caccggagtc tacttgaact ggctgatgtc ccaatgctta       480
tcgctcggcg ccacggtggt taacgtcga gtgaaccata tcaaggatgc aattttcta        540 cactcctcag gatcacgccc cgacgtgatt gtcaactgta gtggtctctt tgcccggttc       600
ttgggaggcg tcgaggacaa gaagatgtac cctattcgag acaagtcgt ccttgttcga       660 aactctcttc cttttatggc ctccttttcc agcactcctg aaaaagaaaa tgaagacgaa       720
gctctatata tcatgacccg attcgatggt acttctatca ttggcggttg tttccaatcc       780
aacaactggt catccgaacc cgatccttct ctcacccatc gaatcctgtc tagagccctc       840
gaccgattcc cggaactgac caaagatggc cctcttgaca ttgtgcgcga atgcgttggc       900
caccgtcctg gtagagaggg cggtccccga gtagaattag agaagatccc cggcgttggc       960
tttgttgtcc ataactatgg tgccgccggt gctggttacc agtcctctta cggcatggct      1020
gatgaagctg tttcttacgt cgaaagagct cttactcgtc caaacctta g              1071

<210> SEQ ID NO 6
<211> LENGTH: 356
<212> TYPE: PRT
```

<213> ORGANISM: Trigonopsis variabilis

<400> SEQUENCE: 6

```
Met Ala Lys Ile Val Val Ile Gly Ala Gly Val Ala Gly Leu Thr Thr
1               5                   10                  15
Ala Leu Gln Leu Leu Arg Lys Gly His Glu Val Thr Ile Val Ser Glu
                20                  25                  30
Phe Thr Pro Gly Asp Leu Ser Ile Gly Tyr Thr Ser Pro Trp Ala Gly
            35                  40                  45
Ala Asn Trp Leu Ser Phe Tyr Asp Gly Gly Lys Leu Ala Asp Tyr Asp
        50                  55                  60
Ala Val Ser Tyr Pro Ile Leu Arg Glu Leu Ala Arg Ser Ser Pro Glu
65                  70                  75                  80
Ala Gly Ile Arg Leu Ile Asn Gln Arg Ser His Val Leu Lys Arg Asp
                85                  90                  95
Leu Pro Lys Leu Glu Gly Ala Met Ser Ala Ile Cys Gln Arg Asn Pro
            100                 105                 110
Trp Phe Lys Asn Thr Val Asp Ser Phe Glu Ile Ile Glu Asp Arg Ser
        115                 120                 125
Arg Ile Val His Asp Asp Val Ala Tyr Leu Val Glu Phe Ala Ser Val
130                 135                 140
Cys Ile His Thr Gly Val Tyr Leu Asn Trp Leu Met Ser Gln Cys Leu
145                 150                 155                 160
Ser Leu Gly Ala Thr Val Val Lys Arg Arg Val Asn His Ile Lys Asp
                165                 170                 175
Ala Asn Phe Leu His Ser Ser Gly Ser Arg Pro Asp Val Ile Val Asn
            180                 185                 190
Cys Ser Gly Leu Phe Ala Arg Phe Leu Gly Gly Val Glu Asp Lys Lys
        195                 200                 205
Met Tyr Pro Ile Arg Gly Gln Val Val Leu Val Arg Asn Ser Leu Pro
210                 215                 220
Phe Met Ala Ser Phe Ser Ser Thr Pro Glu Lys Glu Asn Glu Asp Glu
225                 230                 235                 240
Ala Leu Tyr Ile Met Thr Arg Phe Asp Gly Thr Ser Ile Ile Gly Gly
                245                 250                 255
Cys Phe Gln Ser Asn Asn Trp Ser Ser Glu Pro Asp Pro Ser Leu Thr
            260                 265                 270
His Arg Ile Leu Ser Arg Ala Leu Asp Arg Phe Pro Glu Leu Thr Lys
        275                 280                 285
Asp Gly Pro Leu Asp Ile Val Arg Glu Cys Val Gly His Arg Pro Gly
290                 295                 300
Arg Glu Gly Gly Pro Arg Val Glu Leu Glu Lys Ile Pro Gly Val Gly
305                 310                 315                 320
Phe Val Val His Asn Tyr Gly Ala Ala Gly Ala Gly Tyr Gln Ser Ser
                325                 330                 335
Tyr Gly Met Ala Asp Glu Ala Val Ser Tyr Val Glu Arg Ala Leu Thr
            340                 345                 350
Arg Pro Asn Leu
        355
```

<210> SEQ ID NO 7
<211> LENGTH: 38
<212> TYPE: DNA
<213> ORGANISM: Artificial Sequence
<220> FEATURE:

<223> OTHER INFORMATION: primer for introducing NdeI restriction site

<400> SEQUENCE: 7
tagggctgac atatggctaa aatcgttgtt attggtgc            38

<210> SEQ ID NO 8
<211> LENGTH: 39
<212> TYPE: DNA
<213> ORGANISM: Artificial Sequence
<220> FEATURE:
<223> OTHER INFORMATION: primer for introducing BgIII restriction site

<400> SEQUENCE: 8
tagggctgaa gatctctaaa ggtttggacg agtaagagc           39

<210> SEQ ID NO 9
<211> LENGTH: 33
<212> TYPE: DNA
<213> ORGANISM: Artificial Sequence
<220> FEATURE:
<223> OTHER INFORMATION: forward primer for removing Ampr gene from
      pRSET-A

<400> SEQUENCE: 9
ctgtcagacc aagtttactc atatatactt tag                 33

<210> SEQ ID NO 10
<211> LENGTH: 28
<212> TYPE: DNA
<213> ORGANISM: Artificial Sequence
<220> FEATURE:
<223> OTHER INFORMATION: reverse primer for removing Ampr gene from
      pRSET-A

<400> SEQUENCE: 10
actcttcctt tttcaatatt attgaagc                       28

<210> SEQ ID NO 11
<211> LENGTH: 23
<212> TYPE: DNA
<213> ORGANISM: Artificial Sequence
<220> FEATURE:
<223> OTHER INFORMATION: forward primer for amplifying Kanr gene from
      pET-28b

<400> SEQUENCE: 11
atgagtcata ttcaacggga aac                            23

<210> SEQ ID NO 12
<211> LENGTH: 27
<212> TYPE: DNA
<213> ORGANISM: Artificial Sequence
<220> FEATURE:
<223> OTHER INFORMATION: reverse primer for amplifying Kanr gene from
      pET-28b

<400> SEQUENCE: 12
ttagaaaaac tcatcgagca tcaaatg                        27

<210> SEQ ID NO 13
<211> LENGTH: 2852
<212> TYPE: DNA
<213> ORGANISM: Trigonopsis variabilis

<400> SEQUENCE: 13
gatctcgatc ccgcgaaatt aatacgactc actataggga gaccacaacg gtttccctct   60

-continued

| | |
|---|---|
| agaaataatt ttgtttaact ttaagaagga gatatacata tgcggggttc tcatcatcat | 120 |
| catcatcatg gtatggctag catgactggt ggacagcaaa tgggtcggga tctgtacgac | 180 |
| gatgacgata aggatcgatg gggatccgag ctcgagatct gcagctggta ccatggaatt | 240 |
| cgaagcttga tccggctgct aacaaagccc gaaaggaagc tgagttggct gctgccaccg | 300 |
| ctgagcaata actagcataa ccccttgggg cctctaaacg gtcttgaggg gttttttgc | 360 |
| tgaaaggagg aactatatcc ggatctggcg taatagcgaa gaggcccgca ccgatcgccc | 420 |
| ttcccaacag ttgcgcagcc tgaatggcga atgggacgcg ccctgtagcg gcgcattaag | 480 |
| cgcggcgggt gtggtggtta cgcgcagcgt gaccgctaca cttgccagcg ccctagcgcc | 540 |
| cgctccttc gctttcttcc cttcctttct cgccacgttc gccggctttc cccgtcaagc | 600 |
| tctaaatcgg gggctcccctt tagggttccg atttagtgct ttacggcacc tcgaccccaa | 660 |
| aaaacttgat tagggtgatg gttcacgtag tgggccatcg ccctgataga cggtttttcg | 720 |
| cccctttgacg ttggagtcca cgttctttaa tagtggactc ttgttccaaa ctggaacaac | 780 |
| actcaacccct atcgcggtct attctttga ttttataaggg attttgccga tttcggccta | 840 |
| ttggttaaaa aatgagctga tttaacaaat atttaacgcg aatttaaaca aaatattaac | 900 |
| gcttacaatt taggtggcac ttttcgggga aatgtgcgcg gaaccccctat ttgtttattt | 960 |
| ttctaaatac attcaaatat gtatccgctc atgagacaat aaccctgata aatgcttcaa | 1020 |
| taatattgaa aaaggaagag tatgagtcat attcaacggg aaacgtcttg ctctaggccg | 1080 |
| cgattaaatt ccaacatgga tgctgattta tatgggtata aatgggctcg cgataatgtc | 1140 |
| gggcaatcag gtgcgacaat ctatcgattg tatgggaagc ccgatgcgcc agagttgttt | 1200 |
| ctgaaacatg gcaaaggtag cgttgccaat gatgttacag atgagatggt cagactaaac | 1260 |
| tggctgacgg aatttatgcc tcttccgacc atcaagcatt ttatccgtac tcctgatgat | 1320 |
| gcatggttac tcaccactgc gatccccggg aaaacagcat ccaggtatt agaagaatat | 1380 |
| cctgattcag gtgaaaatat tgttgatgcg ctggcagtgt tcctgcgccg gttgcattcg | 1440 |
| attcctgttt gtaattgtcc ttttaacagc gatcgcgtat ttcgtctcgc tcaggcgcaa | 1500 |
| tcacgaatga ataacggttt ggttgatgcg agtgattttg atgacgagcg taatggctgg | 1560 |
| cctgttgaac aagtctggaa agaaatgcat aaacttttgc cattctcacc ggattcagtc | 1620 |
| gtcactcatg gtgatttctc acttgataac cttattttg acgaggggaa attaataggt | 1680 |
| tgtattgatg ttggacgagt cggaatcgca gaccgatacc aggatcttgc catcctatgg | 1740 |
| aactgcctcg gtgagttttc tccttcatta cagaaacggc ttttcaaaa atatggtatt | 1800 |
| gataatcctg atatgaataa attgcagttt catttgatgc tcgatgagtt tttctaactg | 1860 |
| tcagaccaag tttactcata tatactttag attgatttaa aacttcattt ttaatttaaa | 1920 |
| aggatctagg tgaagatcct ttttgataat ctcatgacca aaatccctta acgtgagttt | 1980 |
| tcgttccact gagcgtcaga ccccgtagaa aagatcaaag gatcttcttg agatcctttt | 2040 |
| tttctgcgcg taatctgctg cttgcaaaca aaaaaaccac cgctaccagc ggtggtttgt | 2100 |
| ttgccggatc aagagctacc aactcttttt ccgaaggtaa ctggcttcag cagagcgcag | 2160 |
| ataccaaata ctgtccttct agtgtagccg tagttaggcc accacttcaa gaactctgta | 2220 |
| gcaccgccta catacctcgc tctgctaatc ctgttaccag tggctgctgc cagtggcgat | 2280 |
| aagtcgtgtc ttaccgggtt ggactcaaga cgatagttac cggataaggc gcagcggtcg | 2340 |
| ggctgaacgg ggggttcgtg cacacagccc agcttggagc gaacgaccta caccgaactg | 2400 |

```
agatacctac agcgtgagct atgagaaagc gccacgcttc ccgaagggag aaaggcggac    2460
aggtatccgg taagcggcag ggtcggaaca ggagagcgca cgagggagct tccagggga     2520 aacgcctggt atctttatag tcctgtcggg tttcgccacc tctgacttga gcgtcgattt    2580
ttgtgatgct cgtcaggggg gcggagccta tggaaaaacg ccagcaacgc ggcctttta     2640 cggttcctgg gcttttgctg gccttttgct cacatgttct ttcctgcgtt atcccctgat    2700
tctgtggata accgtattac cgcctttgag tgagctgata ccgctcgccg cagccgaacg    2760
accgagcgca gcgagtcagt gagcgaggaa gcggaagagc gcccaatacg caaaccgcct    2820
ctccccgcgc gttggccgat tcattaatgc ag                                  2852
```

<210> SEQ ID NO 14
<211> LENGTH: 34
<212> TYPE: DNA
<213> ORGANISM: Artificial Sequence
<220> FEATURE:
<223> OTHER INFORMATION: outer primer for amplifying a gene encoding
      D-amino acid oxidase

<400> SEQUENCE: 14

```
tagggctgac atatggctaa aatcgttgtt attg                                34
```

<210> SEQ ID NO 15
<211> LENGTH: 32
<212> TYPE: DNA
<213> ORGANISM: Artificial Sequence
<220> FEATURE:
<223> OTHER INFORMATION: outer primer for amplifying a gene encoding
      D-amino acid oxidase

<400> SEQUENCE: 15

```
tagggctgaa gatctctaaa ggtttggacg ag                                  32
```

<210> SEQ ID NO 16
<211> LENGTH: 39
<212> TYPE: DNA
<213> ORGANISM: Artificial Sequence
<220> FEATURE:
<223> OTHER INFORMATION: inner forward primer for introducing a mutant
      of amino acidresidue from Thr to Pro at position 53 of SEQ ID
      NO:2

<400> SEQUENCE: 16

```
gcaggtgcca actggctccc gttttacgat ggaggcaag                           39
```

<210> SEQ ID NO 17
<211> LENGTH: 24
<212> TYPE: DNA
<213> ORGANISM: Artificial Sequence
<220> FEATURE:
<223> OTHER INFORMATION: inner reverse primer

<400> SEQUENCE: 17

```
gagccagttg gcacctgccc aagg                                           24
```

<210> SEQ ID NO 18
<211> LENGTH: 39
<212> TYPE: DNA
<213> ORGANISM: Artificial Sequence
<220> FEATURE:

```
<223> OTHER INFORMATION: inner forward primer for introducing a mutant
      of amino acidresidue from Thr to Ser at position 53 of SEQ ID
      NO:2

<400> SEQUENCE: 18
gcaggtgcca actggctcag cttttacgat ggaggcaag                              39
```

RECOMBINANT D-AMINO ACID OXIDASES

FIELD OF THE INVENTION

The present invention belongs to a field of biotechnology and, more specifically, relates to the preparation and use of novel D-amino acid oxidases that have higher catalytic activity and are suitable for the conversion of cephalosporin C to glutaryl-7-aminocephalosporanic acid.

BACKGROUND OF THE INVENTION

7-Aminocephalosporanic acid (7-ACA), the core of many semi-synthetic cephalosporins, is conventionally manufactured chemically from cephalosporin C. The chemical process uses chemical reagents that are highly toxic and heavily pollute the environment and the chemical process is low in conversion rate, as the process requires multiple steps of reactions. Bio-process offers an attractive alternative for the production of 7-ACA. The bioconversion of cephalosporin C to 7-ACA is conducted in two steps: (1) cephalosporin C is first oxidized by D-amino acid oxidase to glutaryl-7-ACA; (2) the glutaryl-7-ACA is then cleaved at the bond between the glutaryl moiety and the 7-ACA moiety by glutaryl-7ACA acylase to 7-ACA. *Rhodotorula gracilis* and *Trigonopsis variabilis* are the two major sources of D-amino acid oxidase for industrial application. However, these enzymes are low in their catalytic activities for oxidizing cephalosporin C (Simonetta, et al., *Biochim. Biophys. Acta,* 914: 136-142 (1987); U.S. Pat. Nos. 5,453,374; and 5,208,155). It is, therefore, desirable for the industry to have a D-amino acid oxidase of higher catalytic activity to reduce the cost of the bioconversion of cephalosporin C to 7-ACA.

SUMMARY OF THE INVENTION

The object of the invention is to provide two recombinant D-amino acid oxidases with higher catalytic activities to oxidize cephalosporin C. Another object of the invention is to apply the recombinant D-amino acid oxidases for the efficient conversion of cephalosporin C to glutaryl-7-aminocephalosporanic acid.

This invention cloned a gene for encoding *T. variabilis* FA10 D-amino acid oxidase (the wild-type; Li, W. et al., *Acta Microbiologica Sinica,* 31:251-253, 1991) into a suitable expression vector and performed the site-directed mutagenesis of the gene to generate a novel D-amino acid oxidase with higher catalytic activity. More specifically, the site-directed mutagenesis was targeted at the 53rd amino acid residue of the peptide in order to generate recombinant D-amino acid oxidases with higher catalytic activities.

In one aspect, the present invention provides a DNA sequence for encoding a recombinant D-amino acid oxidase, which is characterized by a nucleotide variation in comparison to the SEQ ID NO.: 1; resulting in that the amino acid residue at position 53 (i.e. threonine) of the peptide encoded therefrom is replaced by other natural amino acids, and that catalytic activity for oxidizing cephalosporin C, which is used as a substrate, is at least 25% higher; preferably, at least 35% higher; more preferably, at least 50% higher; and most preferably, at least 100% higher than that of its wild-type D-amino acid oxidase.

Preferably, the DNA sequence of the present invention includes the nucleic acid sequence for encoding the peptide sequence as shown in SEQ ID NO.:4 or SEQ ID NO.:6, More preferably, the DNA sequence includes the nucleic acid sequence as shown in SEQ ID NO.: 3 or SEQ ID NO.:5.

In another aspect, the present invention provides a polypeptide characterized in that, with SEQ ID NO.: 2 as a reference sequence, the amino acid residue corresponding to the threonine at position 53 of the reference sequence is changed to other natural amino acids, and that its catalytic activity for oxidizing cephalosporin C is at least 25% higher; preferably, at least 35% higher; more preferably, at least 50% higher; and most preferably, at least 100% higher than that of the wild-type D-amino acid oxidase.

Preferably, the present invention provides a polypeptide characterized in that, with SEQ ID NO.: 2 as the reference sequence, the amino acid residue corresponding to the threonine at position 53 of the reference sequence is serine or proline. In the Examples of the present invention, two novel recombinant D-amino acid oxidases, recombinant D-amino acid oxidase GHA and recombinant D-amino acid oxidase GHB, are provided. Recombinant D-amino acid oxidase GHA has an amino acid sequence as shown in SEQ ID NO.: 4 and its catalytic activity is 105% higher than that of the wild-type D-amino acid oxidase. The recombinant D-amino acid oxidase GHB has an amino acid sequence as shown in SEQ ID NO.: 6 and its catalytic activity is 35% higher than that of the wild-type D-amino acid oxidase. In the present invention, the wild-type D-amino acid oxidase gene refers to the one derived from the D-amino acid oxidase gene of *Trigonopsis variabilis* FA10 (Li, W. et al., *Acta Microbiologica Sinica,* 31:251-253, 1991). The nucleic acid of the wild-type D-amino acid oxidase is shown in SEQ ID NO.: 1 and its amino acid sequence is shown in SEQ ID NO.: 2.

Also covered by the invention are the derivatives of GHA or GHB, including those obtained by conservative substitutions or the addition or deletion of one or more amino acids.

For the preparation of the recombinant D-amino acid oxidases GHA or GHB of the present invention, suitable vectors include, but are not limited to, prokaryotic expression vectors, such as pRSET-A and pET; eukaryotic expression vectors, such as pYD1 and pYES2; and cloning vectors, such as pGEM®-T Easy, pUC18; pUC19 and pBluescript®-SK (+/−).

For the preparation of the novel D-amino acid oxidases of the present invention, either prokaryotic or eukaryotic cells can be employed as host cells. The suitable prokaryotic cells include, but are not limited to, *E. coli, Bacillus subtilis, Bacillus brevis* and *Streptomyces;* and the suitable eukaryotic cells include, but are not limited to, *Saccharomyces cerevisiae, Rhodotorula gracilis, Trigonopsis variabilis, Aspergillus niger, Kluyveromyces lactis* and *Pichia pastoris.*

For the preparation of the novel D-amino acid oxidases GHA or GHB of the present invention, the recombinant D-amino acid oxidases can be readily introduced into appropriate microbial hosts, e.g. *E. coli, S. cerevisiae;* and expressed as intra-cellular or extra-cellular proteins in prokaryotic or eukaryotic cells. Suitable techniques and means for expressing the polypeptide are well known in the art.

In the case in which the recombinant D-amino acid oxidase is expressed as an extra-cellular protein, the enzyme can be partially-purified by conventional biochemical procedures, such as ammonium sulfate fractionation and acetone precipitation, and can be further purified with conventional purification procedures, such as ion exchange and affinity columns. The recombinant D-amino acid oxidase can be used in the form of un-purified/crude extracts, as a partially-purified enzyme, or as a purified enzyme.

In the case in which the recombinant D-amino acid oxidase is expressed as an intra-cellular protein, the enzyme can be purified after the disruption of host cells, followed by centrifugation (to remove cell debris) and fractionation.

For various industrial applications, the recombinant enzymes can be prepared as immobilized cells. Suitable methods or processes for immobilizing enzymes or cells expressing the enzymes are well known to those skilled in the field and may be used. Immobilized cells can be prepared by immobilizing transformed cells containing the recombinant D-amino acid oxidase of the present invention into or onto a solid support or carrier according to the known immobilization methodologies in the art. In the present invention, crude enzyme preparation, partially-purified enzyme preparation, or completely purified preparation of the recombinant D-amino acid oxidase can also be immobilized onto a solid support or carrier using conventional methodologies. Immobilized enzymes can be prepared by adsorption of the recombinant D-amino acid oxidase of the present invention onto an ion-exchange resin.

In addition, the recombinant enzymes can also be prepared as crystal enzymes, as described by Miyake, Y., Aki, K., Hashimoto, S., Yamano, T., *Biochim. Biophys. Acta*, 105:86-99, 1965, The use of the immobilized enzymes and/or crystal enzymes is also within the scope of the present invention.

BRIEF DESCRIPTION OF THE DRAWINGS

FIG. 2 shows the DNA sequence of plasmid pRSET-kan.

PREFERRED EMBODIMENT

Enzymes such as restriction enzymes, T4 DNA ligase, DNA polymerase, and other materials, were obtained from commercial suppliers and used in accordance with manufacturers' instructions. DNA cloning, transformation of host cells, and other procedures are well known in the art or can be adapted from literature.

The following examples are given for the purpose of illustrating this invention but are not limited thereto. Unless indicated in the following examples, conventionally known conditions were adopted or the procedures are performed as recommended by the manufacturer, especially when some specific conditions are not given.

EXAMPLE 1

Construction of a Recombinant Vector pRSET-A-DAO for Expressing *T. variabilis* D-Amino Acid Oxidase Sequence-specific primers were designed in accordance with the known sequences of the 5'- and 3'-ends of the *T. variabilis* D-amino acid oxidase gene (Gonzalez, F. J., Montes, J., Martin, F., Lopez, M. C., Ferminan, E., Catalan, J., Galan, M. A. and Dominguez, A., Molecular cloning of TvDAO1; a gene encoding a D-amino acid oxidase from *Trigonopsis variabilis* and its expression in *Saccharomyces cerevisiae* and *Kluyveromyces lactis*. *Yeast* 13:1399-1408, 1997). The primer pair is shown as follows:

5'-NdeI (incorporated NdeI restriction site)
5'-TAGGGCTGA
CATATGGCTAAAATCGTTGTTATTGGTGC-3' (SEQ ID NO.: 7)
3'-BglII (incorporated BglII restriction site)
5'-TAGGGCTGA
AGATCTCTAAAGGTTTGGACGAGTAAGAGC-3' (SEQ ID NO.: 8)

*T. variabilis* D-amino acid oxidase gene was synthesized by PCR, in which plasmid pJL (Yang, Y. L. et al., Patent Application Publication number: CN1371999A, 2002) was a template. The above-mentioned primer pair and Pfu DNA polymerase (Promega) were used to amplify the gene. Plasmid pJL contains *T. variabilis* FA10 D-amino acid oxidase gene (Li, W. et al., *Acta Microbiologica Sinica*, 31:251-253, 1991). The PCR mixture contained 40 ng pJL, 0.4 µM 5'-NdeI, 0.4 µM 3'-BglII, 50 µM dATP, 50 µM dTTP, 50 µM dCTP, 50 µM dGTP, 20 mM Tris-HCl (pH8.8), 10 mM KCl, 10 mM $(NH_4)_2SO_4$, 2 mM $MgSO_4$, 0.1% Triton X-100; and 2.5 U Pfu DNA polymerase; and the volume of the mixture was made up to 50 µL with sterile deionized water.

PCR profile was as follows:

As a result, a PCR fragment of 1,098 bp was obtained, with NdeI and BglII at the 5'- and 3'-ends respectively. The PCR product was resolved in a 1% agarose gel, purified and cut with NdeI and BglII, then ligated to a 2.9 kb restricted fragment obtained by digesting plasmid pRSET-A (Invitrogen) with NdeI and BglII, so as to generate plasmid pRSET-A-DAO. The plasmid was transformed into a competent *E. coli* BL21(DE3)pLysS (Novagen). The transformants were spread onto LB/amp agar plate and incubated at 37° C. overnight. Plasmid was extracted in accordance with the procedures described in Molecular Cloning—A Laboratory Manual, ed. by J. Sambrook, et al., 1989; CSHL Press. The plasmid was sequenced and confirmed to be *T. variabilis* D-amino acid oxidase gene (see SEQ ID NO.: 1). Its deduced amino acid sequence is shown in as SEQ ID NO.:2.

EXAMPLE 2

Construction of Plasmid pRSET-kan
To remove the ampicillin resistance gene from pRSET-A, the following primers were synthesized based on the sequence of pRSET-A:
VET-F
5'-CTGTCAGACCAAGTTTACTCATATATACTTTAG-3' (SEQ ID NO.:9)
VET-R
5'-ACTCTTCCTTTTTCAATATTATTGAAGC-3' (Sequence 10)
To amplify the kanamycin resistance gene from plasmid pET-28b (Novagen), the following primers were synthesized based on the sequence of pET-28b:

KAN-F
5'-ATGAGTCATATTCAACGGGAAAC-3' (SEQ ID NO.:11)
KAN-R
5'-TTAGAAAAACTCATCGAGCATCAAATG-3' (SEQ ID NO.:12)

The PCR mixture for amplifying pRSET-A fragment devoid of ampicillin resistance gene contained: 50 ng pRSET-A, 0.4 µM VET-F, 0.4 µM VET-R, 50 µM dATP, 50 µM dTTP, 50 µM dCTP, 50 µM dGTP, 20 mM Tris-HCl (pH8.8), 10 mM KCl, 10 mM (NH$_4$)$_2$SO$_4$, 2 mM MgSO$_4$, 0.1% Triton X-100; and 2.5 U Pfu DNA polymerase; and the volume of the mixture was made up to 50 µL with sterile deionized water. The PCR mixture for amplifying the kanamycin resistance gene from plasmid pET-28b contained: 50 ng pET-28b, 0.4 µM KAN-F, 0.4 µM KAN-R, 50 µM dATP, 50 µM dTTP, 50 µM dCTP, 50 µM dGTP, 20 mM Tris-HCl (pH8.8), 10 mM KCl, 10 mM (NH$_4$)$_2$SO$_4$, 2 mM MgSO$_4$, 0.1% Triton X-100; and 2.5 U Pfu DNA polymerase; and the volume of the mixture was made up to 50 µL with sterile deionized water.

Figure 1:
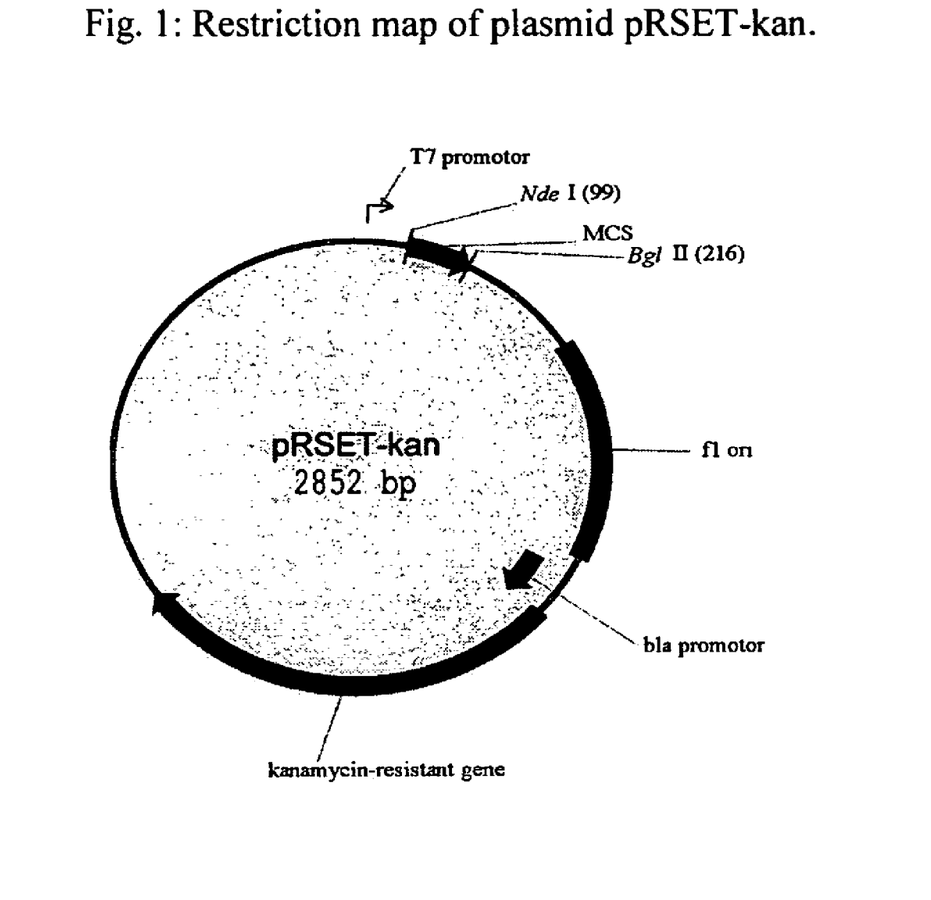
FIG. 1 is the restriction map of plasmid pRSET-kan.

PCR profile was as follows:

The two PCR products (pRSET-A fragment devoid of ampicillin resistance gene, 2,036 bp in size; kanamycin resistance gene, 816 bp in size) were resolved in 1% agarose and purified and ligated to each other. As a result, plasmid pRSET-kan (shown in FIG. 1) was obtained. The plasmid was transformed into a competent E. coli BL21(DE3)pLysS (Novagen) and the transformants were spread onto LB/kan agar plate and incubated at 37° C. overnight. The plasmid was extracted and sequenced. The sequence was shown as FIG. 2 and SEQ ID NO.:13.

EXAMPLE 3

Construction of Recombinant D-Amino Acid Oxidase GHA

Recombinant D-amino acid oxidase GHA was constructed by site-directed mutagenesis, which was based on the procedures in PCR Protocols (Ed. John M. S. Bartlett and David Stirling, Totowa, N.J.: Humana Press, 2003).

Primers were synthesized on the basis of the sequence of the cloned T. variabilis D-amino acid oxidase SEQ ID NO.:1):
Primer A:
5'-TAGGGCTGA
CATATGGCTAAAATCGTTGTTATTG-3' (SEQ ID NO.:14)
Primer B:
5'-TAGGGCTGAAGATCTCTAAAGGTTTGGACGAG-3' (SEQ ID NO.:15)
Primer C1:
5'-GCAGGTGCCAACTGGCTCCCGTTTTAC-GATGGAGGCAAG-3' (SEQ ID NO.:16)
Primer D:
5'-GAGCCAGTTGGCACCTGCCCAAGG-3' (SEQ ID NO.:17)

Primers A and B are a pair of outer primers. Primer A contains NdeI restriction site, with a portion of nucleotides overlapping with the 5'-end of the D-amino acid oxidase gene. Primer B contains BglII restriction site, with a portion of nucleotides overlapping with the 3'-end of the D-amino acid oxidase gene. Primers C1 and D are a pair of inner primers. Primer C1 converts the 53rd amino acid residue of wild-type D-amino acid oxidase from threonine (Thr) to proline (Pro). Primer D contains a portion of nucleotides overlapping with primer C1.

With pRSET-A-DAO as a template, primers A and D were used to perform PCR to synthesize fragment 1; and primers B and C1 were used to synthesize fragment 2, The PCR mixture contained: 20 ng pRSET-A-DAO, 20 mM Tris-HCl (pH8.8), 10 mM KCl, 10 mM (NH$_4$)$_2$SO$_4$, 2 mM MgSO$_4$, 0.1% Triton X-100, 0.4 µM primer A and 0.4 µM primer D (for synthesizing fragment 1) or 0.4 µM primer B and 0.4 µM primer C1 (for synthesizing fragment 2), 50 µM dATP, 50 µM dTTP, 50 µM dCTP, 50 µM dGTP, 1.5 U Pfu DNA polymerase, the volume of the mixture was made up to 50 µL with sterile deionized water.

The PCR profile was as follows:

The amplified fragment 1 and fragment 2 were resolved in and purified from 1% agarose and were used to generate the full-length D-amino acid oxidase gene. The PCR mixture for synthesizing the full-length gene contained: 20 ng fragment 1, 20 ng fragment 2, 20 mM Tris-HCl (pH8.8), 10 mM KCl, 10 mM (NH$_4$)$_2$SO$_4$, 2 mM MgSO$_4$, 0.1% Triton X-100, 0.4 µM primer A and 0.4 µM primer B, 50 µM dATP, 50 µM dTTP, 50 µM dCTP, 50 µM dGTP, 1.5 U Pfu DNA polymerase, the volume of the mixture was made up to 50 µL with sterile deionized water.

The PCR profile was as follows:

As a result, the full-length recombinant D-amino acid oxidase GHA gene was obtained. The gene was cut with NdeI and BglII and then inserted into pRSET-kan, generating pRSET-kan-DAOGHA. The plasmid was transformed into a competent E. coli BL21(DE3)pLysS (Novagen). The resulted transformants were spread onto LB/kan agar plate and incubated at 37° C. overnight. Plasmid was extracted, and the insert was sequenced and confirmed as recombinant D-amino acid oxidase GHA. The DNA sequence for encoding GHA was shown in S SEQ ID NO.:3 and the deduced amino acid sequence was shown in S SEQ ID NO.:4.

EXAMPLE 4

Construction of Recombinant D-Amino Acid Oxidase GHB

Recombinant D-amino acid oxidase was constructed by site-directed mutagenesis, which is based on the procedures in PCR Protocols (Ed. John M. S. Bartlett and David Stirling, Totowa, N.J.: Humana Press, 2003).

Primers were synthesized on the basis of the sequence of the cloned *T. variabilis* D-amino acid oxidase (SEQ ID NO.: 1):
Primer A:
5'-TAGGGCTGA<u>CATATG</u>GCTAAAATCGTTGTTATTG-3' (Sequence 14)
Primer B:
5'-TAGGGCTGA<u>AGATCT</u>CTAAAGGTTTGGACGAG-3' (Sequence 15)
Primer C2:
5'-GCAGGTGCCAACTGGCTCAGCTTTTAC-GATGGAGGCAAG-3' (Sequence 18)
Primer D:
5'-GAGCCAGTTGGCACCTGCCCAAGG-3' (SEQ ID NO.: 17)

The above primers A, B and D were identical as in Example 3, Primer C2 is an inner primer, which converts the 53rd amino acid residue of wild-type D-amino acid oxidase from threonine (Thr) to serine (Ser). Primer D contains a portion of nucleotides overlapping with primer C2, Amplification of fragment 1 was identical as in Example 3. Fragment 3 was amplified by PCR, using pRSET-A-DAO, as a template, and primers B and C2, The PCR mixture contained: 20 ng pRSET-A-DAO, 20 mM Tris-HCl (pH8.8), 10 mM KCl, 10 mM $(NH_4)_2SO_4$, 2 mM $MgSO_4$, 0.1% Triton X-100, 0.4 µM primer B and 0.4 µM primer C2, 50 µM dATP, 50 µM dTTP, 50 µM dCTP, 50 µM dGTP, 1.5 U Pfu DNA polymerase, the volume of the mixture was made up to 50 µL with sterile deionized water.

The PCR profile was as follows:

The amplified fragment 1 and fragment 3 were resolved in and purified from 1% agarose and were used to generate the full-length D-amino acid oxidase gene GHB. The PCR mixture for synthesizing the full-length gene GHB contained: 20 ng fragment 1, 20 ng fragment 3, 20 mM Tris-HCl (pH8.8), 10 mM KCl, 10 mM $(NH_4)_2SO_4$, 2 mM $MgSO_4$, 0.1% Triton X-100, 0.4 µM primer A and 0.4 µM primer B, 50 µM dATP, 50 µM dTTP, 50 µM dCTP, 50 µM dGTP, 1.5 U Pfu DNA polymerase, the volume of the mixture was made up to 50 µL with sterile deionized water.

The PCR profile was as follows:

As a result, the full-length recombinant D-amino acid oxidase GHB gene was obtained. The gene was cut with NdeI and BglII and then inserted into pRSET-kan. The resultant plasmid was transformed into a competent *E. coli* BL21 (DE3)pLysS (Novagen). The transformants were spread onto LB/kan agar plate and incubated overnight at 37° C. The plasmid was extracted, and the insert was sequenced and confirmed as recombinant D-amino acid oxidase GHB. The DNA sequence for encoding GHB was shown in SEQ ID NO.:5 and the deduced amino acid sequence was shown in SEQ ID NO.:6.

EXAMPLE 5

Purification of D-Amino Acid Oxidase

Figure 3:
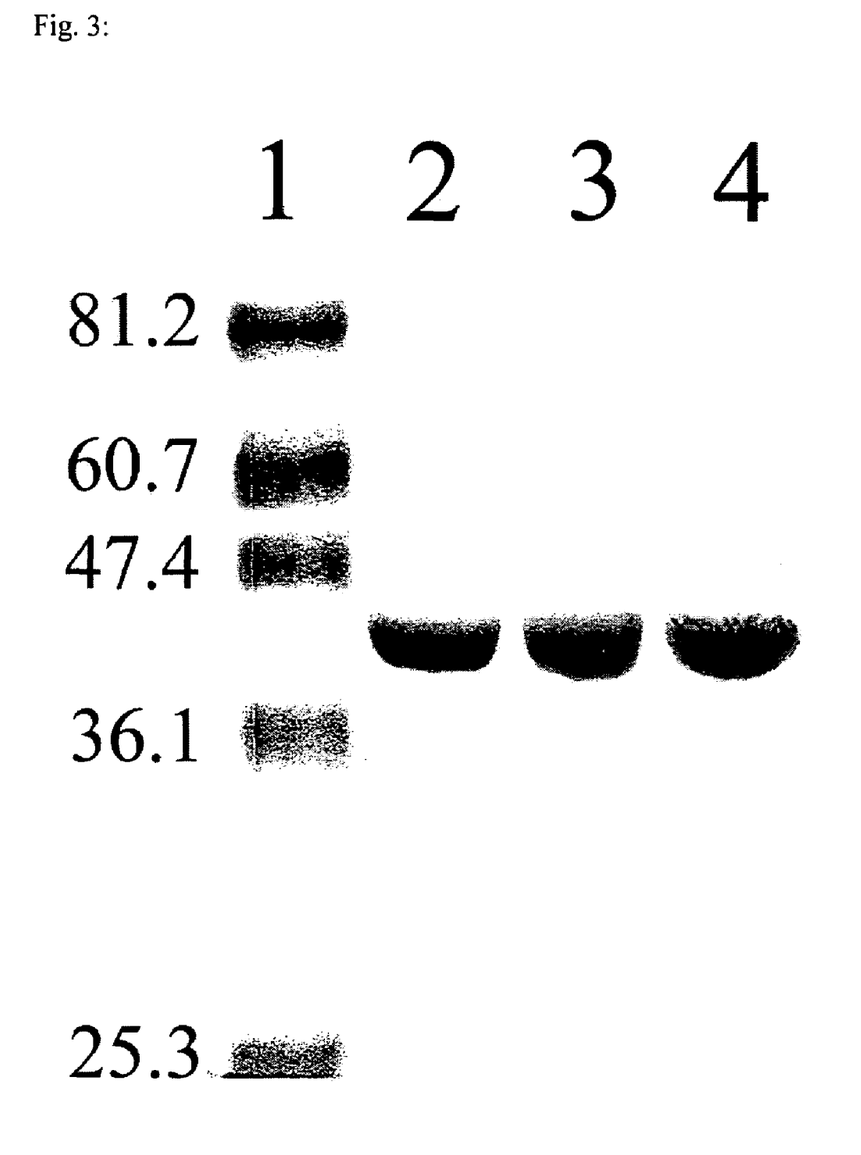
FIG. 3 is a photograph of the SDS-PAGE eletrophoresis of the recombinant D-amino acid oxidases GHA and GHB. Lane I shows BenchMark™ Pre-Stained Protein Ladder (Invitrogen) with protein sizes in kDa. Lane 2 shows the electrophoresis result of *T. variabilis* FA10 D-amino acid oxidase. Lane 3 shows the electrophoresis result of D-amino acid oxidase GHA. Finally, lane 4 shows the electrophoresis result of D-amino acid oxidase GHB.

The purification of D-amino acid oxidase was essentially performed in accordance with Alonso, J., Barredo, J. L., Diez, B., Mellado, E., Salto, F., Garcia, J. L., Cortes, E. (D-amino acid oxidase gene from *Rhodotorula gracilis* [*Rhodosporidium toruloides*] ATCC 26217, *Microbiology* 144:1095-1101, 1998). A single colony of pRSET-kan-DAOGHA containing *E. coli* BL21(DE3)pLysS (Example 3) was inoculated and cultivated in 200 mL LB medium supplemented with ampicillin at 250 rpm for 12 hours. Following this, 1 mM IPTG was added and it was then induced for another 6 hours. The bacterial cells were pelleted and resuspended in 20 mL Buffer A [20 mM sodium phosphate buffer (pH8.0) containing 20% glycerol, 5 mM 2-mercaptoethanol, 1 mM PMSF and 2 mM EDTA], disrupted with ultrasonication, and centrifuged at 13,000 g for 20 min at 4° C. to collect the supernatant as crude D-amino acid oxidase. The crude D-amino acid oxidase was applied to DEAE-cellulose (Sigma, 6×2.5 cm), eluted by Buffer A. The eluate was considered as partially-purified recombinant D-amino acid oxidase GHA. The partially-purified recombinant D-amino acid oxidase GHA can be further purified by the following method: the partially-purified recombinant D-amino acid oxidase GHA is applied to Buffer A-equilibrated Cibacron Blue 3GA-sepharose (Pharmacia LKB Biotechnology, 4×1 cm), washed by 30 mL 1M sodium phosphate (pH8), followed by elution with 10 mL Buffer A containing 50 µM FAD. The purity of the protein was analyzed by SDS-PAGE (FIG. 3). *T. variabilis* D-amino acid oxidase and recombinant D-amino acid oxidase GHB were also extracted and purified in accordance with the above-described procedures (FIG. 3).

EXAMPLE 6

Determination of Activity of D-Amino Acid Oxidase

The procedures were performed in accordance with Isogai, T., Ono, H., Ishitani, Y., Kojo, H., Ueda, Y. and Kohsaka, M. (Structure and expression of cDNA for D-amino acid oxidase active against cephalosporin C from *Fusarium solani*. *J. Biochem*, [Tokyo] 108:1063-1069, 1990), with modifications made to a particular step. Three mL sodium phosphate (50 mM, pH7.5) with 75 mM cephalosporin C sodium was combined with 3 mL partially-purified *T. variabilis* D-amino acid oxidase (Example 5) to prepare a reaction mixture. The mixture was oxygenated and vortexed at 22° C. for 60 min. Aliquots (100 µL) were withdrawn at different times (1, 5, 10, 30, 60 min), mixed with 10 µL 3% hydrogen peroxide, and 50 µL 10% trichloroacetic acid was added to stop the reaction. The mixture was centrifuged (10,000 g, 3 min) and 10 µL of supernatant was mixed with 990 µL HPLC mobile phase and then it was analyzed by HPLC. HPLC column: Diamonsil™ C18, 250×4.6 mm (Beijing); mobile phase: 50 mM $K_2HPO_4$/$KH_2PO_4$ (pH7.0), 5% acetonitrile; column temperature: 30° C.; flow rate: 1 mL/min; scanning: 260 nm UV. One unit of enzyme activity was defined as the amount of enzyme that converted 1 µmole of cephalosporin C to glutary-7-aminocephalosporanic acid per minute under the above reaction condition. The activities of recombinant D-amino acid oxidase GHA and recombinant D-amino acid oxidase GHB were also determined by the above-mentioned method. The activity of the recombinant D-amino acid oxidase GHA was determined as 205% of that of the wild-type *T. variabilis* D-amino acid oxidase; the activity of the recombinant D-amino acid oxidase GHB was determined 135% of that of the wild-type T. variabilis D-amino acid oxidase.

EXAMPLE 7

Preparation of Immobilized D-Amino Acid Oxidase

Extraction and purification of the D-amino acid oxidase was performed in accordance with Example 5, Preparation of the immobilized D-amino acid oxidase was performed in accordance with the description from Rohm (Darmstadt, Germany). A 50 mL partially-purified recombinant D-amino acid oxidase GHA solution (containing 200 mg total protein) was added to $K_2HPO_4$ and $KH_2PO_4$ in order to adjust it to contain 0.5M phosphate with a pH of 7.5, Five g dry Eupergit™ C (Röhm GmBH, Darmstadt, Germany), was added into the enzyme solution, stirred (75 rpm) at room temperature (17° C.-23° C.) for 72 hours and then filtered to remove the supernatant. The resultant immobilized enzyme was washed several times by deionized distilled water and collected by filtration. The total immobilized enzyme generated was 19.4 g. The activity of the immobilized recombinant D-amino acid oxidase GHA was determined in the same way as described in Example 6; with the exception of using 19.4 g of immobilized recombinant D-amino acid oxidase GHA in a reaction volume of 1,000 mL. The activity of the immobilized recombinant D-amino acid oxidase GHA was 65 units/g wet carrier.

This invention is not limited by the detailed description provided in the Examples above. Various modifications can be made by those skilled in the field and these modifications should be also regarded as being within the scope of the invention, which is defined by the claims.

We claim:

1. A recombinant D-amino acid oxidase characterized by the proline residue or serine residue at position 53 of the wild-type D-amino acid oxidase having the amino acid sequence as shown in SEQ ID NO: 2, and characterized by its catalytic activity for oxidizing cephalosporin C which is at least 25% higher than that of the wild-type D-amino acid oxidase having the amino acid sequence as shown in SEQ ID NO: 2.

2. The recombinant D-amino acid oxidase according to claim 1, wherein the oxidase has the amino acid sequence of SEQ ID NO: 4.

3. The recombinant D-amino acid oxidase according to claim 2, wherein the amino acid sequence is encoded by the nucleotide sequence of SEQ ID NO: 3.

4. The recombinant D-amino acid oxidase according to claim 1, wherein the oxidase has the amino acid sequence of SEQ ID NO: 6.

5. The recombinant D-amino acid oxidase according to claim 4, wherein the amino acid sequence is encoded by the nucleotide sequence of SEQ ID NO: 5.

6. An isolated DNA molecule comprising the nucleotide sequence encoding the recombinant D-amino acid oxidase of claim 1.

7. The isolated DNA sequence according to claim 6, wherein said DNA sequence encodes the amino acid sequence of SEQ ID NO: 4.

8. The isolated DNA sequence according to claim 7, wherein said DNA sequence comprises the nucleotide sequence of SEQ ID NO: 3.

9. The isolated DNA sequence according to claim 6, wherein said DNA sequence encodes the amino acid sequence of SEQ ID NO: 6.

10. The isolated DNA sequence according to claim 9, wherein said DNA sequence comprises the nucleotide sequence of SEQ ID NO: 5.

11. A vector comprising the DNA sequence according to claims 6.

* * * * *